US012373707B2

(12) United States Patent
Zhang

(10) Patent No.: US 12,373,707 B2
(45) Date of Patent: Jul. 29, 2025

(54) MEDICAL KNOWLEDGE GRAPHS FOR USE IN AN INTELLIGENT DIAGNOSTIC ASSISTANT

(71) Applicant: BOE TECHNOLOGY GROUP CO., LTD., Beijing (CN)

(72) Inventor: Zhenzhong Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 1215 days.

(21) Appl. No.: 17/033,438

(22) Filed: Sep. 25, 2020

(65) Prior Publication Data
US 2021/0192365 A1    Jun. 24, 2021

(30) Foreign Application Priority Data
Dec. 19, 2019    (CN) .......................... 201911316849.9

(51) Int. Cl.
 *G06N 5/025* (2023.01)
 *G06N 5/022* (2023.01)
 *G16H 10/60* (2018.01)
 *G16H 50/20* (2018.01)

(52) U.S. Cl.
 CPC ............. *G06N 5/025* (2013.01); *G06N 5/022* (2013.01); *G16H 10/60* (2018.01); *G16H 50/20* (2018.01)

(58) Field of Classification Search
 CPC ........ G06N 5/022; G06N 5/025; G16H 10/60; G16H 50/20
 See application file for complete search history.

(56) References Cited

U.S. PATENT DOCUMENTS

| 8,965,818 B2 * | 2/2015 | Zillner | G16H 50/20 |
| | | | 706/14 |
| 2009/0024615 A1 * | 1/2009 | Pedro | G06F 16/367 |
| | | | 707/999.005 |

(Continued)

OTHER PUBLICATIONS

Rotmensch et al., "Learning a Health Knowledge Graph from Electronic Medical Records," Scientific Reports, Jul. 20, 2017, pp. 1-11. (Year: 2017).*

(Continued)

*Primary Examiner* — Eric J. Bycer
(74) *Attorney, Agent, or Firm* — McDermott Will & Emery LLP

(57) ABSTRACT

The present disclosure provides a computer device, a system, a readable storage medium, and a medical data analysis method. The method includes: acquiring symptom information of a patient and examination result information of a patient; accessing a predetermined knowledge graph; determining an initial weight of each of the plurality of first nodes and the plurality of second nodes of the predetermined knowledge graph according to the above-mentioned information; transmitting evidence through the plurality of edges on the predetermined knowledge graph based on the initial weight of each of the plurality of first nodes and the plurality of second nodes, to determine a final weight of each node on the knowledge graph; and determining prediction information for the symptom information of the patient and the examination result information of the patient based on the final weight of each node.

15 Claims, 3 Drawing Sheets

(56) References Cited

U.S. PATENT DOCUMENTS

| | | | | |
|---|---|---|---|---|
| 2011/0112380 A1* | 5/2011 | Robinson | ............... | G16H 50/20 |
| | | | | 600/300 |
| 2011/0295790 A1* | 12/2011 | Zillner | .................... | G06N 5/02 |
| | | | | 706/55 |
| 2016/0180215 A1* | 6/2016 | Vinyals | .................. | G06N 3/045 |
| | | | | 706/20 |
| 2016/0188570 A1* | 6/2016 | Lobez Comeras | ..... | G06F 40/40 |
| | | | | 704/9 |
| 2017/0011183 A1* | 1/2017 | Valverde, Jr. | ......... | G06F 40/169 |
| 2017/0277855 A1* | 9/2017 | De La Torre | ........... | G16Z 99/00 |
| 2017/0277856 A1* | 9/2017 | De La Torre | ....... | G06F 16/9024 |
| 2018/0089382 A1* | 3/2018 | Allen | .................... | G06F 40/205 |
| 2018/0122509 A1* | 5/2018 | Christiansson | ........ | G16H 50/30 |
| 2018/0144424 A1* | 5/2018 | Sahu | ..................... | G16H 10/20 |
| 2018/0218126 A1* | 8/2018 | Salazar | .................. | G16H 50/30 |
| 2018/0322954 A1* | 11/2018 | Ding | .................... | G16H 70/60 |
| 2019/0057316 A1* | 2/2019 | Zhang | .................... | G16H 50/30 |
| 2019/0252074 A1* | 8/2019 | Datla | .................... | G06F 17/10 |
| 2020/0051692 A1* | 2/2020 | Wang | .................... | G16H 70/60 |
| 2020/0073976 A1* | 3/2020 | Lecue | .................. | G06F 16/245 |
| 2020/0075139 A1* | 3/2020 | Master | .................. | G16H 10/20 |
| 2020/0117857 A1* | 4/2020 | Gnanasambandam | ...................... | |
| | | | | G16H 10/20 |
| 2020/0219618 A1* | 7/2020 | Wang | ..................... | G06F 40/20 |

OTHER PUBLICATIONS

De la Villa et al., "A Learning Support Tool with Clinical Cases Based on Concept Maps and Medical Entity Recognition," ACM, IUI 2012, Feb. 14-17, 2012, pp. 61-70. (Year: 2012).*

* cited by examiner

MEDICAL KNOWLEDGE GRAPHS FOR USE IN AN INTELLIGENT DIAGNOSTIC ASSISTANT

CROSS-REFERENCE TO RELATED APPLICATION

This application claims the benefit of Chinese Patent Application No. 201911316849.9 filed on Dec. 19, 2019, the entire contents of which are hereby incorporated by reference.

TECHNICAL FIELD

The present disclosure relates to the field of computer technology, and particularly to a computer device, a system, a readable storage medium, and a medical data analysis method.

BACKGROUND

The application of an auxiliary diagnosis system based on disease prediction may reduce the labor intensity of doctors and improve work efficiency. Especially for young doctors at the grassroots level, it may not only help them achieve more accurate judgments, but also help people better manage their health.

SUMMARY

The purpose of the present disclosure is to provide a computer device, system, readable storage medium, and medical data analysis method.

According to an aspect of the present disclosure, there is provided a medical data analysis method based on a medical knowledge graph, executed by a computer device, the method comprising: acquiring symptom information of a patient and examination result information of a patient; accessing a predetermined knowledge graph, the predetermined knowledge graph comprises a plurality of nodes and a plurality of edges, the plurality of nodes comprise a plurality of first nodes configured to characterize multiple types of symptoms, a plurality of second nodes configured to characterize multiple types of examination results, and a plurality of third nodes configured to characterize multiple types of diseases, the plurality of edges are configured to characterize relationships between the symptoms and the diseases, and relationships between the diseases and the examination results; determining an initial weight of each of the plurality of first nodes and the plurality of second nodes of the predetermined knowledge graph according to the symptom information and the examination result information; transmitting evidence through the plurality of edges on the predetermined knowledge graph based on the initial weight of each of the plurality of first nodes and the plurality of second nodes, to determine a final weight of each of the plurality of nodes; and determining prediction information for the symptom information and the examination result information based on the final weight of each of the plurality of nodes.

For example, the determining an initial weight of each of the plurality of first nodes and the plurality of second nodes of the predetermined knowledge graph according to the symptom information and the examination result information comprises: for a first node in the plurality of first nodes for a confirmed symptom in the symptom information and a second node in the plurality of second nodes for a confirmed examination result in the examination result information, an initial weight is set to q; for a first node in the plurality of first nodes for a denial symptom in the symptom information and a second node in the plurality of second nodes for a denial examination result in the examination result information, an initial weight is set to $\alpha_2$; and for other first nodes in the plurality of first nodes except the first node for the confirmed symptom and for the denial symptom, and other second nodes in the plurality of second nodes except the second node for the confirmed examination result and for the denial examination result, an initial weight is set to $\alpha_3$.

For example, the values of $\alpha_1$, $\alpha_2$, and $\alpha_3$ are respectively set as $\alpha_1=1$, $\alpha_2=-1$, $\alpha_3=0$.

For example, the transmitting evidence through the plurality of edges on the predetermined knowledge graph based on the initial weight of each of the plurality of first nodes and the plurality of second nodes, to determine a final weight of each of the plurality of nodes comprises: performing iterative calculation on the weight of each of the plurality of nodes using a random walk algorithm based on the initial weight of each of the plurality of first nodes and the plurality of second nodes to realize that the symptom information and the examination result information are served as initial evidences to be transmitted through the plurality of edges on the predetermined knowledge graph, so as to determine a final weight of each of the plurality of nodes.

For example, the performing iterative calculation on the weight of each of the plurality of nodes using a random walk algorithm comprises: performing iterative calculation on the weight of each of the plurality of nodes according to the following formula to determine the final weight of each of the plurality of nodes:

for a $j_{th}$ third node $d_j$ in the plurality of third nodes, an initial weight is:

$$S_0(d_j) = \lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right);$$

a weight calculated in the $(t+1)^{th}$ iteration is:

$$S_{t+1}(d_j) = (1-\lambda)S_t(d_j) + \lambda \left( \sum_{i=1}^{I} S_t(s_i) \times \frac{e_{i,j}}{\sum_{j=1}^{J} e_{i,j}} + \sum_{k=1}^{K} S_t(c_k) \times \frac{e_{k,j}}{\sum_{j=1}^{J} e_{k,j}} \right);$$

for a $i_{th}$ first node $s_i$ in the plurality of first nodes, a weight calculated in the $(t+1)^{th}$ iteration is:

$$S_{t+1}(s_i) = (i-\lambda)S_t(s_i) + \lambda \sum_{j=1}^{J} S_t(d_j) \times \frac{e_{i,j}}{\sum_{i=1}^{I} e_{i,j}};$$

for a $k_{th}$ second node $c_k$ in the plurality of second nodes, a weight calculated in the $(t+1)^{th}$ iteration is:

$$S_{t+1}(c_k) = (i-\lambda)S_t(c_k) + \lambda \sum_{j=1}^{J} S_t(d_j) \times \frac{e_{k,j}}{\sum_{k=1}^{K} e_{k,j}};$$

wherein t=0,1, ..., T−1; $\lambda$ is a predetermined harmonic parameter; $S_0(s_i)$ is an initial weight of the first node $s_i$; $S_0(c_k)$ is an initial weight of the second node $c_k$; when there is an edge between the first node $s_i$ and the third node $d_j$, then e is set to 1, when there is no edge between the first node $s_i$ and the third node $d_j$, then $e_{i,j}$ is set to 0; when there is an edge between the second node $c_k$ and the third node $d_j$, the $e_{k,j}$ is set to 1, when there is no edge between the second node $c_k$ and the third node $d_j$, the $e_{k,j}$ is set to 0; I, K, J is the number of the plurality of first nodes, the number of the plurality of second nodes, and the number of the plurality of third nodes, respectively.

For example, the value of the harmonic parameter $\lambda$ is set to $\Delta \in (0,1)$.

For example, the termination condition of the iterative calculation comprises: reaching maximum number of iterations (T); or the rate of change of the weight of each of the plurality nodes is lower than a predetermined threshold. For example, the value of the maximum number T of iterations can be set to T=10000.

For example, the determining prediction information for the symptom information and the examination result information based on the final weight of each of the plurality of nodes comprises: sorting the plurality of third nodes according to the final weight in a descending order, and outputting disease information for the top N third nodes as the prediction information for the symptom information and the examination result information; or sorting the plurality of third nodes according to the final weight in an ascending order, and outputting disease information for third nodes ranked in the bottom N as the prediction information for the symptom information and the examination result information; wherein N is a positive integer.

For example, the determining prediction information for the symptom information and the examination result information based on the final weights of the plurality of nodes comprises: determining second nodes in the plurality of second nodes that are for the examination result not contained in the examination result information as candidate second nodes; sorting the candidate second nodes according to the final weight in a descending order, and outputting the examination information for the top M candidate second nodes as the prediction information for the symptom information and the examination result information; or sorting the candidate second nodes according to the final weight in an ascending order, and outputting the examination information for the candidate second nodes ranked as bottom M as the prediction information for the symptom information and the examination result information; wherein M is a positive integer.

For example, prior to acquiring symptom information and examination result information of a patient, the method further comprises: extracting symptom information, disease information, examination result information, relationship information between the symptoms and the diseases, and a relationship information between the diseases and the examination results from medical data; constructing the plurality of first nodes, the plurality of third nodes, and the plurality of second nodes based on the symptom information, the disease information, and the examination result information, and constructing the plurality of edges among the plurality of nodes based on the relationship information between the symptoms and diseases and the relationship information between the diseases and the examination results, so that the predetermined knowledge graph is formed by the plurality of nodes and the plurality of edges.

According to another aspect of the present disclosure, there is provided a computer device comprising a memory, a processor, and a computer program stored on the memory and running on the processor, wherein the processor is configured to execute the following steps when the computer program is loaded: acquiring symptom information of a patient and examination result information of a patient; accessing a predetermined knowledge graph, the predetermined knowledge graph comprises a plurality of nodes, the plurality of nodes comprise a plurality of first nodes configured to characterize multiple types of symptoms, a plurality of second nodes configured to characterize multiple types of examination results, a plurality of third nodes configured to characterize multiple types of diseases, and a plurality of edges configured to characterize the relationship between symptoms and diseases, and the relationship between diseases and examination results; determining an initial weight of each of the plurality of first nodes and the plurality of second nodes of the predetermined knowledge graph according to the symptom information and the examination result information; transmitting evidence through the plurality of edges on the predetermined knowledge graph based on the initial weight of each of the plurality of first nodes and the plurality of second nodes, to determine a final weight of each of the plurality of nodes; and determining prediction information for the symptom information and the examination result information based on the final weights of each of the plurality of nodes.

For example, the processor is configured to execute the following steps when the computer program is loaded: for a first node in the plurality of first nodes for a confirmed symptom in the symptom information and a second node in the plurality of second nodes for a confirmed examination result in the examination result information, an initial weight is set to $\alpha_1$; for a first node in the plurality of first nodes for a denial symptom in the symptom information and a second node in the plurality of second nodes for a denial examination result in the examination result information, an initial weight is set to $\alpha_2$; and for other first nodes in the plurality of first nodes except the first node for the confirmed symptom and for the denial symptom, and other second nodes in the plurality of second nodes except the second node for the confirmed examination result and for the denial examination result, an initial weight is set to $\alpha_3$.

For example, the values of $\alpha_1$, $\alpha_2$ and $\alpha_3$ are respectively set as $\alpha_1=1$, $\alpha_2=-1$, $\alpha_{3=0}$.

For example, the processor is configured to execute the following step when the computer program is loaded: performing iterative calculation on the weight of each of the plurality of nodes using a random walk algorithm based on the initial weight of each of the plurality of first nodes and the plurality of second nodes to realize that the symptom information and the examination result information are served as initial evidences to be transmitted through the plurality of edges of evidence on the predetermined knowledge graph, so as to determine a final weight of each of the plurality of nodes.

For example, when the computer program is loaded, the processor is configured to execute: performing iterative calculation on the weight of each of the plurality of nodes according to the following formula to determine the final weight of each node:

for a $j^{th}$ third node $d_j$ in the plurality of third nodes, an initial weight is:

$$S_0(d_j) = \lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right);$$

a weight calculated in the $(t+1)^{th}$ iteration is:

$$S_{t+1}(d_j) = (1-\lambda)S_t(d_j) + \lambda \left( \sum_{i=1}^{I} S_t(s_i) \times \frac{e_{i,j}}{\sum_{j=1}^{J} e_{i,j}} + \sum_{k=1}^{K} S_t(c_k) \times \frac{e_{k,j}}{\sum_{j=1}^{J} e_{k,j}} \right);$$

for a $i^{th}$ first node $s_i$ in the plurality of first nodes, a weight calculated in the $(t+1)^{th}$ iteration is:

$$S_{t+1}(s_i) = (i-\lambda)S_t(s_i) + \lambda \sum_{j=1}^{J} S_t(d_j) \times \frac{e_{i,j}}{\sum_{i=1}^{I} e_{i,j}};$$

for a $k^{th}$ second node $c_k$ in the plurality of second nodes, a weight calculated in the $(t+1)^{th}$ iteration is:

$$S_{t+1}(c_k) = (i-\lambda)S_t(c_k) + \lambda \sum_{j=1}^{J} S_t(d_j) \times \frac{e_{k,j}}{\sum_{k=1}^{K} e_{k,j}};$$

wherein $t=0,1,\ldots,T-1$; $\lambda$ is a predetermined harmonic parameter; $S_0(s_i)$ is an initial weight of the first node $s_i$; $S_0(c_k)$ is an initial weight of the second node $c_k$; when there is an edge between the first node $s_i$ and the third node $d_j$, the $e_{i,j}$ is set to 1, when there is no edge between the first node $s_i$ and the third node $d_j$, the $e_{i,j}$ is set to 0; when there is an edge between the second node $c_k$ and the third node $d_j$, the $e_{k,j}$ is set to 1, when there is no edge between the second node $c_k$ and the third node $d_j$, the $e_{k,j}$ is set to 0; I, K, J is the number of the plurality of first nodes, the number of the plurality of second nodes, and the number of the plurality of third nodes, respectively.

For example, the value of the harmonic parameter $\lambda$ is set to $\lambda \in (0,1)$.

For example, the termination condition of the iterative calculation comprises:

reaching maximum number of iterations (T); or the rate of change of the weight of each of the plurality nodes is lower than a predetermined threshold. In one embodiment, the value of the maximum number T of iterations can be set to T=10000.

For example, when the computer program is loaded, the processor is configured to execute: sorting the plurality of third nodes according to the final weight from largest to smallest, and outputting disease information for the top N third nodes as the prediction information for the symptom information and the examination result information; or sorting the plurality of third nodes according to the final weight from smallest to largest, and outputting disease information for third nodes ranked in the bottom N as the prediction information for the symptom information and the examination result information; wherein N is a positive integer.

For example, when the computer program is loaded, the processor is configured to execute: determining second nodes in the plurality of second nodes that are for the examination result not contained in the examination result information as candidate second nodes; sorting the candidate second nodes according to the final weight from largest to smallest, and outputting the examination information for the top M candidate second nodes as the prediction information for the symptom information and the examination result information; or sorting the candidate second nodes according to the final weight from smallest to largest, and outputting the examination information for the candidate second nodes ranked in the bottom M as the prediction information for the symptom information and the examination result information; wherein M is a positive integer.

For example, when the computer program is loaded, the processor is configured to further execute: prior to acquiring symptom information of a patient and examination result information of a patient, extracting symptom information, disease information, examination result information, relationship information between symptoms and diseases, and relationship information between diseases and examination results from medical data; constructing the plurality of first nodes, the plurality of third nodes, and the plurality of second nodes based on the symptom information, the disease information, and the examination result information, and constructing edges among the plurality of nodes based on the relationship information between the symptoms and diseases and the relationship information between the diseases and the examination results, so that the predetermined knowledge graph is formed by the plurality of nodes and the plurality of edges.

According to another aspect of the present disclosure, there is provided a computer system comprising a terminal device and the computer device, the terminal device is configured to send user's symptom information and examination result information to the computer device, and receive output from the computer device.

According to another aspect of the present disclosure, there is provided a non-transitory computer-readable storage medium on which a computer program is stored, wherein the following steps are executed when the computer program is loaded by a processor: acquiring symptom information of a patient and examination result information of a patient; accessing a predetermined knowledge graph, the predetermined knowledge graph comprises a plurality of nodes, the plurality of nodes comprise a plurality of first nodes configured to characterize multiple types of symptoms, a plurality of second nodes configured to characterize multiple types of examination results, a plurality of third nodes configured to characterize multiple types of diseases, and a plurality of edges configured to characterize the relationship between symptoms and diseases, and the relationship between diseases and examination results; determining an initial weight of each of the plurality of first nodes and the plurality of second nodes of the predetermined knowledge graph according to the symptom information and the examination result information; transmitting evidence through the plurality of edges on the predetermined knowledge graph based on the initial weight of each of the plurality of first nodes and the plurality of second nodes, to determine a final weight of each of the plurality of nodes; and determining prediction information for the symptom information and the examination result information based on the final weight of each of the plurality of nodes.

BRIEF DESCRIPTION OF THE DRAWINGS

The specific embodiments of the present disclosure will be described in further detail below in conjunction with the accompanying drawings.

DETAILED DESCRIPTION OF EMBODIMENTS

Figure 1:
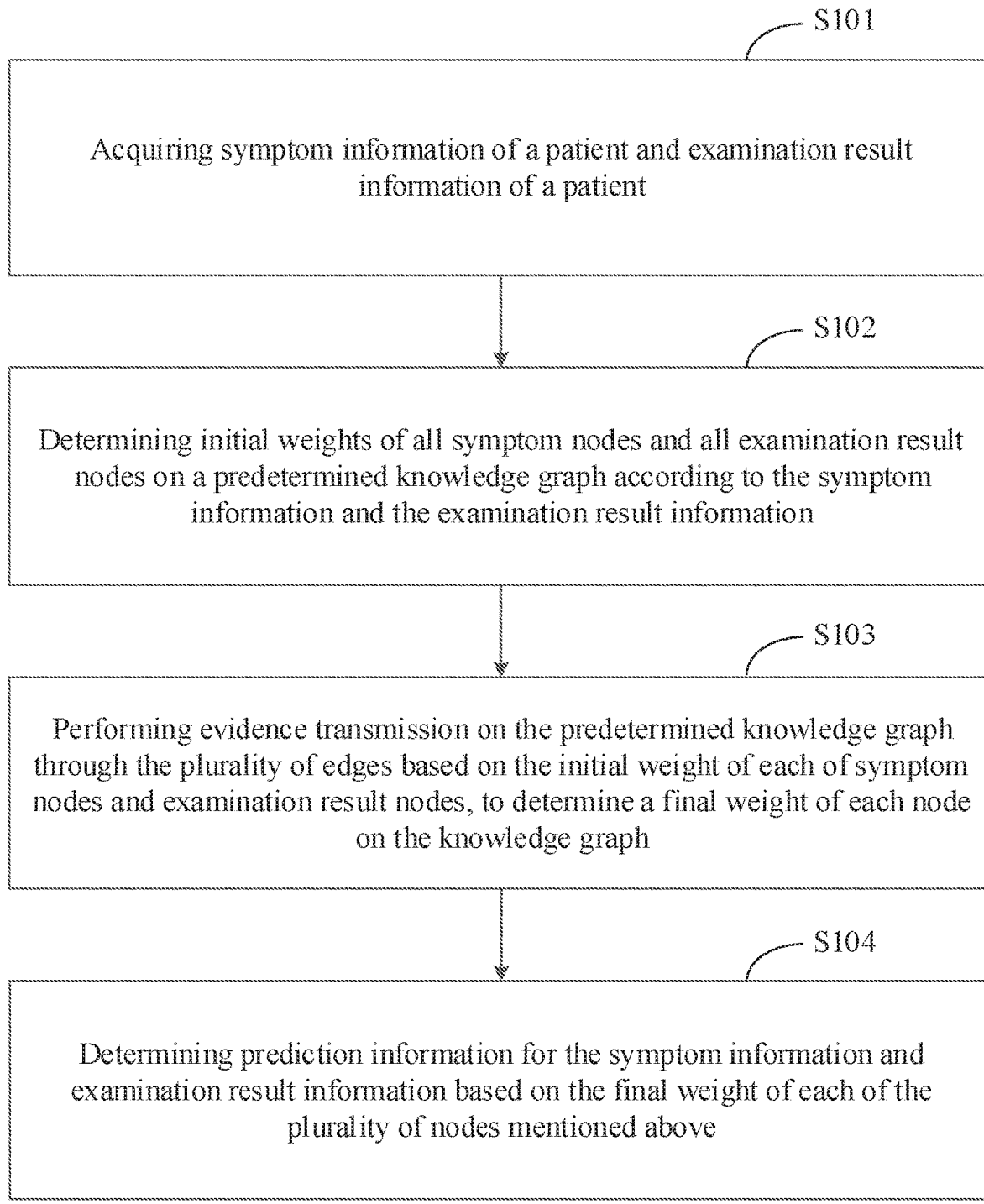
FIG. 1 shows a flowchart of a medical data analysis method based on a medical knowledge graph provided by an embodiment of the present disclosure.

In order to explain the present disclosure more clearly, the following further describes the present disclosure with reference to preferred embodiments and drawings. Similar components in the drawings are denoted by the same reference numerals. Those skilled in the art should understand that the content specifically described below is illustrative rather than restrictive, and should not be used to limit the scope of protection of the present disclosure.

Figure 2:
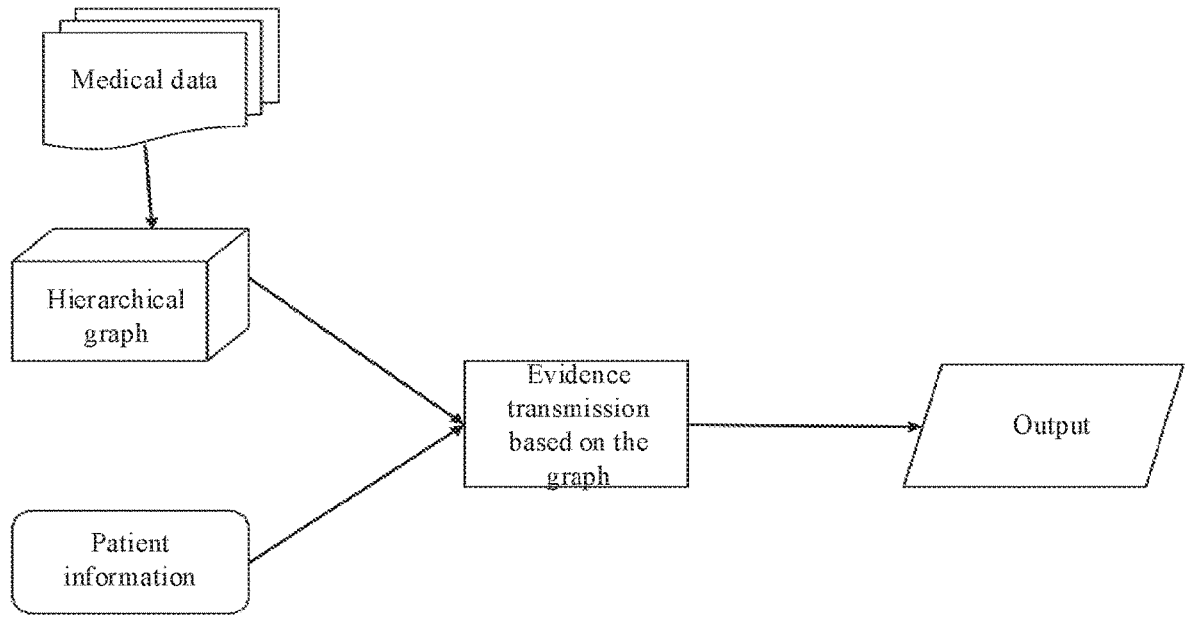
FIG. 2 shows a data trend diagram in a medical data analysis method based on a medical knowledge graph provided by an embodiment of the present disclosure.

The current auxiliary diagnosis system may be roughly divided into two categories: one is the auxiliary diagnosis system based on expert knowledge, and the other is the auxiliary diagnosis system based on the machine learning method. Where the auxiliary diagnosis system based on expert knowledge has a small coverage and is only suitable for auxiliary diagnosis of diseases in specific fields. The common practice of auxiliary diagnosis systems based on machine learning methods is to extract features from data, then train a predictive model through machine learning methods, and finally use the model to make predictions. Auxiliary diagnosis systems based on machine learning methods usually only use the symptoms identified by the patient as features. For example, for the patient's description of "cough, expectoration, no fever", only "cough" and "expectoration" are used as symptom information features to predict. However, in the actual diagnosis, the symptoms that the patient has confirmed to be absent are also very important information when the doctor diagnoses. Therefore, the prediction result of the auxiliary diagnosis system based on the machine learning method is not accurate enough. As shown in FIGS. 1 and 2, an embodiment of the present disclosure provides a medical data analysis method based on a medical knowledge graph. The method may be executed by a processor loading a computer program stored in a memory, and includes the following steps S101~-S104.

In Step S101, acquiring symptom information of a patient and examination result information of a patient.

In Step S102, determining an initial weight of each of a plurality of first nodes and a plurality of second nodes on a predetermined knowledge graph according to the symptom information and the examination result information.

According to an embodiment of the present disclosure, before the step S102, it is necessary to access the predetermined knowledge graph. The predetermined knowledge graph may be pre-stored in the device, or it may be called from other devices or servers, etc. The predetermined knowledge graph includes a plurality of nodes and a plurality of edges. The plurality of nodes may include the plurality of first nodes mentioned above for characterizing multiple types of symptoms, the plurality of second nodes mentioned above for characterizing multiple types of examination results, and a plurality of third nodes for characterizing multiple types of diseases. The plurality of edges may be used to characterize relationships between the symptoms and the diseases, and relationships between the diseases and the examination results. In an embodiment, the first node may be referred to as a symptom node, the second node may be referred to as an examination result node, and the third node may be referred to as a disease node. In the step S102, the initial weights of all symptom nodes and all examination result nodes are determined. It may be understood that the predetermined knowledge graph uses symptoms, diseases, and examination results as nodes, and uses the relationships between the symptoms and the diseases, and the relationships between the diseases and the examination results as edges among nodes.

In Step S103, performing evidence transmission on the predetermined knowledge graph through the plurality of edges based on the initial weight of each of symptom nodes and examination result nodes, to determine a final weight of each node on the knowledge graph, that is, to determine a final weight of each of the plurality of nodes mentioned above.

In Step S104, determining prediction information for the symptom information and examination result information based on the final weight of each of the plurality of nodes mentioned above.

The medical data analysis method based on the medical knowledge graph provided by this embodiment, regardless of whether the information input by the user contains a certain symptom or examination result, whether the contained symptom or the examination result is confirmed or denied, the final weight of each node on the knowledge graph is determined through the transmission of evidence based on all symptoms and all examination results. This may accurately and efficiently provide a basis for patient disease prediction, and provide effective assistance for disease diagnosis. It may be implemented as a general diagnosis auxiliary system covering diseases in various fields according to the computer device that executes the method, and has high application value.

In the example shown in FIG. 2, a hierarchical graph is constructed based on medical data, and the hierarchical graph may be a representation of the knowledge graph predetermined above. After the computer device acquires patient information such as symptom information of the patient and examination result information of the patient, it may use the patient information as initial evidence, and determine the prediction information for the patient information based on the evidence transmission process of the graph as the output of the computer device.

The medical data analysis method based on the medical knowledge graph provided by an embodiment of the present disclosure does not limit the specific way of acquiring the symptom information of the patient and examination result information of the patient. For example, the symptom information and the examination result information may be acquired through user's input, or related information may be directly acquired in the memory.

In a specific example, the process of constructing a predetermined knowledge graph is as follows: extracting symptom information, disease information, examination result information, relationship information between the symptoms and the diseases, and relationship information between the diseases and the examination results from medical data, constructing the plurality of first nodes, the plurality of third nodes, and the plurality of second nodes according to symptom information, disease information, and examination result information, respectively, and constructing edges between nodes according to the relationship information between the symptoms and the diseases and the relationship information between the diseases and the examination results, thereby constructing a knowledge graph. Where the knowledge graph may be embodied in a graph model, and further, may be embodied in the form of a hierarchical graph. Taking the relationship between the symptoms and the diseases, and the relationship between the diseases and the examination results shown in FIG. 3 as examples: extracting symptom information from medical data, such as "fever", "cough", and "expectoration" to construct the plurality of first nodes: "fever" node, "cough" node, and "expectoration" node; extracting disease information from medical data, such as "pneumonia" and "common cold" to construct the plurality of third nodes: "pneumonia" nodes and "common cold" nodes; extracting examination result information from medical data, such as "shadow on chest radiograph" and "routine blood neutrophil percentage>70%" to construct the plurality of second nodes: "shadow on chest radiograph" nodes and "routine blood neutrophil percentage>70%" nodes. According to the medical data, the disease corresponding to the symptom "fever" may be "pneumonia" or "common cold". Therefore, when constructing the knowledge graph, an edge is formed between the "fever" node and the "pneumonia" node, and an edge is formed between the "fever" node and the "common cold" node. According to the medical data, the disease corresponding to the symptom "cough" is also "pneumonia" or the "common cold", and an edge is formed between the "cough" node and the "pneumonia" node, and an edge is formed between the "cough" node and the "common cold" node. In the same way, an edge is also formed between the "expectoration" node and the "pneumonia" node, and an edge is also formed between the "expectoration" node and the "common cold" node. In the same way, according to the medical data, for example, the disease "pneumonia" corresponds to the examination results "shadow on chest radiograph" and "routine blood neutrophil percentage>70%", and when constructing the knowledge map, an edge is formed between the "pneumonia" node and the "shadow on chest radiograph" node, and an edge is formed between the "pneumonia" node and the "routine blood neutrophil percentage>70%" node. This relationship may also be established among other nodes.

Where the medical data may be derived from at least one of the Internet, documents, and medical records.

For example, the Internet may be various medical question-and-answer websites, which use medical professionals to answer medical questions raised by users.

For example, documents may be printed or electronicized various diagnosis and treatment guidelines, doctors' desk manuals, medical books, and medical papers, etc.

For example, the medical record may be a handwritten medical record or an electronic medical record.

Where the evidence transmission on the graph reflects the score transmission. For example, the more relevant the patient's symptom information and examination result information, the higher the score of the disease, which means the greater the likelihood of suffering from the disease. For example, the patient says he has a cough, and the symptom information "cough" is used as the initial evidence. The evidence transmission is preformed through the edges on the knowledge graph, and the possible disease is judged to be a "common cold" or "pneumonia". The patient says that he also has fever, and at this time the symptom information "fever" may be used as an evidence, so as to increase the likelihood that the patient has a "common cold" as a result of the evidence transmission.

In some optional implementations of the embodiments of the present disclosure, the process of determining the initial weights of all symptom nodes and all examination result nodes on the predetermined knowledge graph according to the symptom information and the examination result information may include: for a confirmed symptom in the symptom information and a confirmed examination result in the examination result information, the initial weights of the corresponding first node and second node are set to $\alpha_1$; for a denial symptom in the symptom information and a denial examination result in the examination result information, the initial weights of the corresponding first node and second node are set to $\alpha_2$; for symptoms not contained in the symptom information and examination results not contained in the examination result information, the initial weights of the corresponding first node and second node are set to $\alpha_3$. It is understandable that the values of $\alpha_1$, $\alpha_2$, and $\alpha_3$ are different, respectively.

Where the confirmed symptom in the symptom information is the symptom that the user has confirmed to appear in the symptom information, the denial symptom in the symptom information is the symptom that the user has confirmed not to appear in the symptom information, and the symptom that is not contained in the symptom information is that the user did not mention in the symptom information. For example, if the acquired symptom information is "fever, no expectoration", in the example of the knowledge graph shown in FIG. 3, the "fever" symptom corresponding to the "fever" node is the confirmed symptom in the symptom information, "expectoration" symptom corresponding to the "expectoration" node is a denial symptom in the symptom information, and the "cough" symptom corresponding to the "cough" node is a symptom not contained in the symptom information. Therefore, the initial weight of the "fever" node is set to $\alpha_1$, the initial weight of the "expectoration" node is set to $\alpha_2$, and the initial weight of the "cough" node is set to $\alpha_3$. Similarly, the confirmed examination result in the examination result information is the examination result confirmed by the user that appears in the examination result information, the denial examination result in the examination result information is the examination result confirmed by the user that does not appear in the examination result information, and the examination result not contained in the examination result information is the examination result not mentioned by the user in the examination result information. For example, if the acquired examination result information is "shadow on chest radiograph" and "the routine blood neutrophil percentage is 60%", the examination result of "shadow on chest radiograph" corresponding to the "shadow on chest radiograph" node is the confirmed examination result in the examination result information, the examination result of "the routine blood neutrophil percentage >70%" corresponding to "the routine blood neutrophil percentage >70%" node is the denial examination result in the examination result information, and the examination result of "routine urine PH>8" corresponding to the "routine urine PH>8" node is the examination result not contained in the examination result information on the knowledge graph including "shadow on chest radiograph" node, "the routine blood neutrophil percentage >70%" node, and the "routine urine pH>8" node. Therefore, the initial weight of the "shadow on chest radiograph" node is set to $\alpha_1$, the initial weight of the "the routine blood neutrophil percentage >70%" node is set to $\alpha_2$, and the initial weight of the "routine urine PH>8" node is set to $\alpha_3$.

With this implementation method, performing differentiated initial value setting of the corresponding symptom nodes and examination result nodes for the examination results, confirmed appearing symptoms, confirmed non-appearing symptoms, and unrepresented examination results and symptoms reflected in the symptom information of patient and the examination result information of patient. Therefore, the accuracy and validity of the final weight of each node on the obtained knowledge graph is ensured. It is understandable that if any symptom is not contained in the symptom information, then it means that there is no symptom information or the symptom information is empty. At this time, the follow-up process may only be performed based on the user's examination result information. On the contrary, if the examination result information does not contain any examination result, it means that there is no examination result information or the examination result information is empty. In this case, the follow-up process may be performed only based on the user's symptom information.

In some optional implementations of this embodiment, for example, the values of $\alpha_1$, $\alpha_2$, and $\alpha_3$ are respectively set as $\alpha_1=1$, $\alpha_2=-1$, $\alpha_3=0$.

There may be two reasons for no symptom contained in the symptom information and no examination result contained in the examination result information: one is that the user forgets to put the existing symptoms (whether confirmed or denied) into the symptom information and put the existing examination results (whether confirmed or denied) into the examination result information; the other is that the symptoms or the examination results that are not contained do not exist. Without further information confirmation, the initial weight of this type of node is set to 0, that is, the unknown event is treated as equal probability, the initial weights of the corresponding nodes of the confirmed symptom in the symptom information and the confirmed examination result in the examination result information are set to 1, and the initial weights of the corresponding nodes of the denial symptom in the symptom information and the denial examination result in the examination result information are set to −1, that is the initial weights of the confirmed occurring events and confirmed non-occurring events are set to a positive value of 1 and a negative value of −1, respectively, based on the principle of maximum entropy as a criterion for selecting the statistical characteristics of random variables that best meet the objective situation. Therefore, the accuracy and validity of the final weight of each node on the obtained knowledge graph is ensured.

In some optional implementations of the embodiments of the present disclosure, the evidence is transmitted through the plurality of edges on the predetermined knowledge graph based on the initial weight of each symptom node and each examination result node to determine that the final weight of each node on the knowledge graph may include: performing iterative calculation on the weight of each node using a random walk algorithm based on the initial weight of each symptom node and each examination result node, so as to realize that the symptom information of the patient and the examination result information of the patient are served as initial evidences that transmitted through the evidences of the plurality of edges on the predetermined knowledge graph, and determine a final weight of each node on the knowledge graph.

For example, a random walk algorithm is used to transmit evidence. The random walk algorithm used in this implementation may accurately and efficiently obtain the final weight of each node on the knowledge graph.

In some optional implementations of the embodiments of the present disclosure, the symptom information of the patient and the examination result information of the patient are transmitted through the evidences of the plurality of edges on the predetermined knowledge graph by using the random walk algorithm to iteratively calculate the weight of each node based on the initial weight of each symptom node and each examination result node, so as to determine that the final weight of each node on the knowledge graph may be implemented in the following manner.

Performing iterative calculation on the weight of each node according to the following formula to determine the final weight of each node.

For a $j^{th}$ disease node $d_j$, the initial weight may be expressed as formula (1).

$$S_0(d_j) = \lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right) \quad \text{Formula 1)}$$

It is understandable that the initial weights of all symptom nodes and all examination result nodes of the knowledge graph are determined according to the acquired symptom information and examination result information, while the initial weights of all disease nodes are calculated by this formula according to the initial weights of each symptom node and each examination result node, and the edges representing the relationships between the symptoms and the diseases and the relationships between the diseases and the examination results on the knowledge graph.

For a $j^{th}$ disease node $d_j$ a weight calculated in the $(t+1)^{th}$ iteration may be expressed as formula (2).

$$S_{t+1}(d_j) = (1 - \lambda)S_t(d_j) + \quad \text{Formula (2)}$$
$$\lambda \left( \sum_{i=1}^{I} S_t(s_i) \times \frac{e_{i,j}}{\sum_{j=1}^{J} e_{i,j}} + \sum_{k=1}^{K} S_t(c_k) \times \frac{e_{k,j}}{\sum_{j=1}^{J} e_{k,j}} \right)$$

For a $i^{th}$ symptom node $s_i$ a weight calculated in the $(t+1)^{th}$ iteration may be expressed as formula (3).

$$S_{t+1}(s_i) = (i - \lambda)S_t(s_i) + \lambda \sum_{j=1}^{J} S_t(d_j) \times \frac{e_{i,j}}{\sum_{i=1}^{I} e_{i,j}} \quad \text{Formula (3)}$$

For a $k^{th}$ examination result node $c_k$, a weight calculated in the $(t+1)^{th}$ iteration may be expressed as formula (4).

$$S_{t+1}(c_k) = (i-\lambda)S_t(c_k) + \lambda \sum_{j=1}^{J} S_t(d_j) \times \frac{e_{k,j}}{\sum_{k=1}^{K} e_{k,j}};$$

Formula (4)

In the above formulas (1)~(4): t=0,1, ..., T−1. λ is a predetermined harmonic parameter; $S_0(s_i)$ is an initial weight of the symptom node $s_i$; $S_0(c_k)$ is an initial weight of the examination result node $c_k$; when there is an edge between the symptom node $s_i$ and the disease node $d_j$, then $e_{i,j}$ is set to 1, when there is no edge between the symptom node $s_i$ and the disease node $d_j$, the $e_{i,j}$ is set to 0; when there is an edge between the examination result node $c_k$ and the disease node $d_j$, then $e_{k,j}$ is set to 1, when there is no edge between the examination result node $c_k$ and the disease node $d_j$, the $e_{k,j}$ is set to 0; I, K, J is the number of the plurality of symptom nodes, the number of the plurality of examination result nodes, and the number of the plurality of disease nodes, respectively.

For disease nodes $d_j$, "$(1-\lambda)S_t(d_j)$" may constrain the change range of the disease node $d_j$ after each iteration calculation, or control the change range of the disease node $d_j$ after each iteration calculation within a controllable range to ensure the effective convergence of the random walk algorithm. The $$"\lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right)"$$

may accurately characterize the relationships between diseases and symptoms and the relationships between diseases and examination results. In general, the meaning of the calculation formula of the $S_{t+1}(d_j)$ is: the greater the weight of the symptoms and examination results corresponding to a certain disease, the greater the weight transmitted to the disease.

For symptom nodes $s_i$, "$(1-\lambda)S_t(s_i)$" may constrain the change range of the symptom node $s_i$ after each iteration calculation, or control the change range of the symptom node $s_i$ after each iteration calculation within a controllable range to ensure the effective convergence of the random walk algorithm. The $$"\lambda \sum_{j=1}^{J} S_t(d_j) \times \frac{e_{i,j}}{\sum_{i=1}^{I} e_{i,j}}"$$

may accurately characterize the relationships between symptoms and diseases. In general, the meaning of the calculation formula of the $S_{t+1}(s_i)$ is: the greater the weight of a certain disease (that is, the greater the probability of the patient suffering from the disease), the greater the weight of the symptoms (or related, with "edge" connection) corresponding to the disease.

Figure 3:
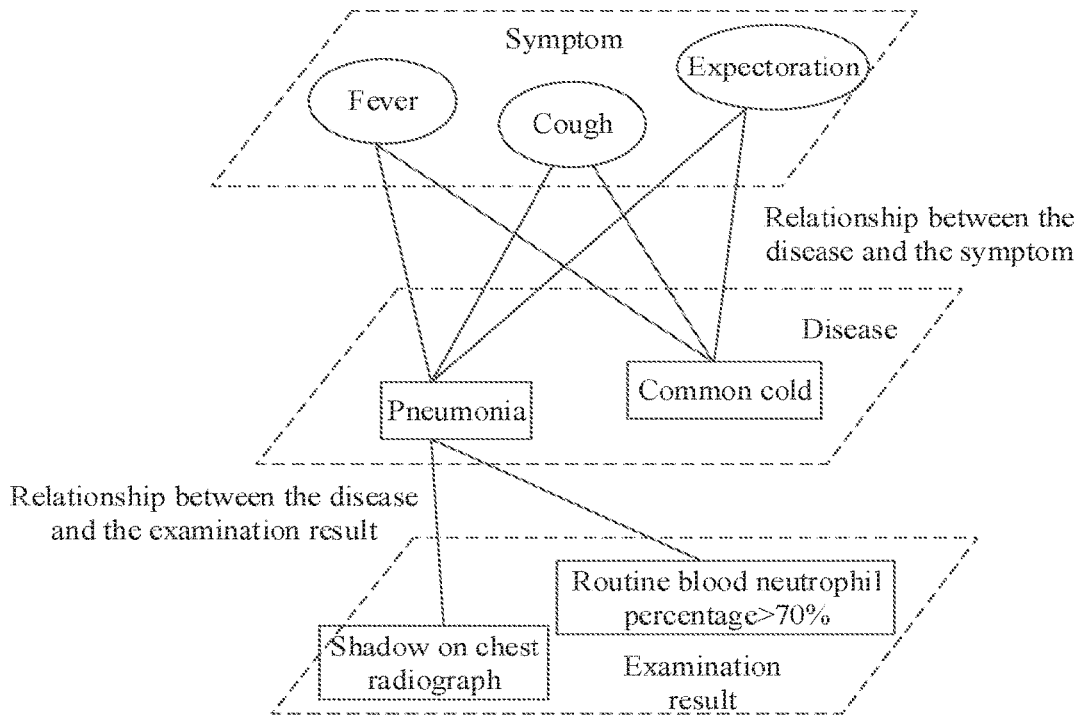
FIG. 3 shows a schematic diagram of a hierarchical graph.

For the examination result node $c_k$, the "$(1-\lambda)S_t(c_k)$" may constrain the change range of the examination result node $c_k$ after each iterative calculation, or control the change range of the examination result node $c_k$ after each iterative calculation within a controllable range to ensure the effective convergence of the random walk algorithm. The $$"\lambda \sum_{j=1}^{J} S_t(d_t) \times \frac{e_{k,n}}{\sum_{k=1}^{K} e_{k,j}}"$$

may accurately characterize the relationships between the examination results and the diseases. In general, the meaning of the calculation formula of the $S_{t+1}(c_k)$ is: the greater the weight of a certain disease (that is, the greater the probability of the patient suffering from the disease), the greater the weight of the examination results (or related, with "edge" connection) corresponding to the disease. For example, the hierarchical graph as shown in FIG. 3, if the probability of a patient suffering from pneumonia is high, the possibility of a shadow on the chest radiograph will also be high, and if the probability of the patient having a common cold is high, the possibility of a shadow on the chest radiograph will be small. As there is no edge between the "common cold" node and the "shadow on chest radiograph" node, that is, the "$e_{k,j}$" between the "common cold" node and the "shadow on chest radiograph" node is equal to 0, and the weight of the "common cold" node may not be passed to "shadow on chest radiograph" node.

With reference to the above, it may be seen that in the calculation formulas of $S_{t+1}(d_j)$, $S_{t+1}(s_i)$, and $S_{t+1}(c_k)$, the overall function of the harmonic parameter λ is to control the weight of the current iteration calculation and the proportion of the weight passed by the nodes of other layers in the relationships.

In summary, with this implementation manner, it may ensure the accuracy and efficiency of the iterative calculation performed on the weight of each node through the random walk algorithm. The iterative calculation formula may accurately characterize the relationships between the symptoms and the diseases and the relationships between the diseases and the examination results, and the random walk algorithm may effectively converge, so that the final weight of each node on the knowledge graph may be accurately and efficiently obtained.

In addition, for the above mentioned iterative calculation formulas, it may be set that $$S_t(s) = \begin{bmatrix} s_{1,t} \\ \ldots \\ s_{I,t} \end{bmatrix}, S_t(c) = \begin{bmatrix} c_{1,t} \\ \ldots \\ c_{K,t} \end{bmatrix}, S_t(d) = \begin{bmatrix} d_{1,t} \\ \ldots \\ d_{J,t} \end{bmatrix},$$

where, $s_{i,t}$ represents the score of the symptom node $s_i$ in the $t^{th}$ iteration, $d_{j,t}$ represents the score of the disease node $d_j$ in the $t^{th}$ iteration, and $c_{k,t}$ represents the score of the examination result node $c_k$ in the $t^{th}$ iteration, and a matrix form of the above mentioned formulas is as follows.

For the symptom nodes: $S_{t+1}(s) = \lambda \times A \times S_t(d) + (1-\lambda)S_t(s)$ where A is a matrix of I×J, $$A_{i,j} = \frac{e_{i,j}}{\sum_{i=1}^{I} e_{i,j}},$$

and $e_{i,j}$ represents the weight of the edge between the symptom node $s_i$ and the disease node $d_j$.

For the disease nodes: $S_{t+1}(d)=(1-\lambda)\times S_t(d)+\lambda\times B\times S_t(s)+\lambda\times C\times S_t(c)$, where B is a matrix of J×I, $$B_{j,i} = \frac{e_{j,i}}{\sum_{j=1}^{J} e_{j,i}},$$

$e_{j,i}$ represents the weight of the edge between the disease node $d_j$ and the symptom node $s_i$, it should be noted that, $e_{i,j}=e_{j,i}$; C is a matrix of J×K, $$C_{j,k} = \frac{e_{j,k}}{\sum_{j=1}^{J} e_{j,k}},$$

$e_{j,k}$ represents the weight of the edge between the disease node $d_j$ and the examination result node $c_k$.

For the examination result node: $S_{t+1}(c)=(1-\lambda)\times S_t(c)+\lambda\times G\times S_t(d)$, where G is a matrix of K×J, $$G_{k,j} = \frac{e_{k,j}}{\sum_{k=1}^{K} e_{k,j}},$$

$e_{k,j}$ represents the weight of the edge between the examination result node $c_k$ and the disease node $d_j$.

In some optional implementations of the embodiments of the present disclosure, the value of the harmonic parameter $\lambda$ is set $\lambda\in(0,1)$ Further, the value of the harmonic parameter $\lambda$ is set to $\lambda=0.5$.

The value of the harmonic parameter $\lambda$ set in this implementation may ensure the accuracy of the iterative calculation formula and the effective convergence of the random walk algorithm.

In some optional implementations of the embodiments of the present disclosure, the termination condition of the iterative calculation is that the maximum number of iterations is reached or the weight of each node does not change. For example, when the rate of change of the weight of each of the plurality of nodes on the knowledge graph is lower than a predetermined threshold, it means that the iterative calculation has reached convergence and reached the termination condition.

The termination condition of the iterative calculation set by this optional implementation may ensure the accuracy of the iterative calculation formula and effective convergence of the random walk algorithm.

In some optional implementations of the embodiments of the present disclosure, for example, the value of the maximum number T of iterations is set to T=10000.

In this implementation, the maximum number T=10000 of iterative calculations is set to be the appropriate value based on the number of nodes and the number of edges on the hierarchical graph covering each medical field, which may ensure the efficiency of the calculation while ensuring the accuracy. It is understandable that if it is only applied to a certain medical field, when the number of nodes and the number of edges is small, the value of the maximum number of iteration calculations may be reduced accordingly.

In some optional implementations of the embodiments of the present disclosure, determining prediction information for the symptom information of the patient and the examination result information of the patient based on the final weight of each node on the knowledge graph in the above mentioned step S104 may include: sorting the final weight of each disease node in a descending order, and outputting the disease information corresponding to the top N disease nodes; or sorting the final weight of each disease node in an ascending order, and outputting the disease information corresponding to the last N disease nodes. Where N is a positive integer.

This implementation may intuitively provide a basis for the patient's disease prediction, and is beneficial to effectively assist in the diagnosis of the disease. For example, only the disease information corresponding to the disease node with the largest final weight may be output as the basis for disease prediction. For example, in a case that the weight of the disease node with the largest final weight is significantly greater than that of other disease nodes, N=1 may be set, that is, only the disease information corresponding to the disease node with the largest final weight is output as the basis for disease prediction; in the case that the weight of the disease node with the largest final weight is closer to the final weight of at least one other disease node, N>1 may be set.

In some optional implementations of the embodiments of the present disclosure, the determining prediction information for the symptom information of the patient and the examination result information of the patient based on the final weight of each node on the knowledge graph in the above mentioned step S104 may also include: sorting the final weight of each of the examination result nodes corresponding to the examination results not contained in the examination result information in a descending order, and outputting the examination result information corresponding to the top M examination result nodes; or, sorting the final weight of each of the examination result nodes corresponding to the examination results not contained in the examination result information in an ascending order, and outputting the examination result information corresponding to the last M examination result nodes. Where M is a positive integer.

With this implementation, a basis for the disease prediction of the patient is provided and targeted examination suggestions are intuitively given. In particular, in a case that there are two or more disease nodes with the largest final weight, and the weight of the disease node with the largest final weight is close to the final weight of at least one other disease node, at this point, although the reference of the basis provided for the disease prediction is insufficient, the supplementary targeted examination suggestions may effectively guide patients to conduct more targeted examinations.

In a specific example, the graph model (hierarchical graph) is shown in FIG. 3. The value of the harmonic parameter $\lambda$ is set to $\lambda=0.5$. The information input by the user is "fever, cough, and no expectoration" (there is no mention of chest radiograph examination and routine blood examination). The initial weights of the symptom nodes and examination result nodes on the hierarchical graph are set as follows: "fever" node and "cough" node are the nodes corresponding to the confirmed symptoms in the symptom information, and the initial weight is set to 1; the "expectoration" node is the node corresponding to the denial symptom in the symptom information, and the initial weight is set to −1; the "shadow on chest radiograph" node and "the routine blood neutrophil percentage >70%" node are the nodes corresponding to the examination results not contained in the examination result information, and the initial weight is set to 0. According to the formula (1) in this embodiment, the initial weight of the "pneumonia" node is $S_0(d_1)=0.5\times(1\times\frac{1}{2}+1\times\frac{1}{2}-1\times\frac{1}{2}+0+0)=0.25$, where the weight of the "fever" node passed to the "pneumonia" node is ½. This is due to the presence of edge between the "fever" node and the "pneumonia" node and the presence of edge between the "fever" node and the "common cold" node. Therefore, when calculating the initial weight of the "pneumonia" node, the weight that the "fever" node passes to the "pneumonia" node is $$S_0(s_i) \times \frac{e_{i,j}}{\sum_{j=1}^{J} e_{i,j}} = 1 \times \frac{1}{1+1} = \frac{1}{2}.$$

In the same way, the weight passed from the "cough" node to the "pneumonia" node is ½, and the weight passed from the "expectoration" node to the "pneumonia" node is −½, the weight passed from the "shadow on chest radiograph" node and "the routine blood neutrophil percentage >70%" node to the "pneumonia" node is 0; in the same way, the initial weight of the "common cold" node is $S_0(d_2)=0.5\times(1\times\frac{1}{2}+1\times\frac{1}{2}-1\times\frac{1}{2}+0+0)=0.25$. The weight of each disease node (the third node) may be calculated iteratively according to the above formula (2).

After the first iteration of calculation, the weight of the "pneumonia" node becomes: $S_1(d_1)=(1-0.5)\times 0.25+0.5\times(1\times\frac{1}{2}+1\times\frac{1}{2}-1\times\frac{1}{2}+0+0)=0.375$.

The weight of the "common cold" node becomes:

$S_0(d_2)=(1-0.5)\times 0.25+0.5\times$
$(1\times\frac{1}{2}+1\times\frac{1}{2}-1\times\frac{1}{2}+0+0)=0.375$.

The weight of the "shadow on chest radiograph" node becomes:

$S_1(c_1)=(1-0.5)\times 0+0.5\times(0.25\times 1)=0.125$.

The weight of the "the routine blood neutrophil percentage >70%" node becomes:

$S_1(c_2)=(1-0.5)\times 0+0.5\times(0.25\times 1)=0.125$.

In the above mentioned weight results, as the weight of the "pneumonia" node is the same as the weight of the "common cold" node, a basis of whether the patient has pneumonia or a common cold may not be given based on that the information input by the user is "fever, cough, and no expectoration" (there is no mention of chest radiograph examination and routine blood examination). At this point, the "chest radiograph" examination, "routine blood" examination, and other examinations may be output for further confirmation. For example, the examination suggestions for "chest radiograph" may be output. If the user inputs the information that the chest radiograph has shadows after the chest radiograph has been examined, the weight of the "shadow on chest radiograph" node may become 1, and back to the above mentioned process, "the initial weight of the "pneumonia" node becomes $S_0(d_1)=0.5\times(1\times\frac{1}{2}+1\times\frac{1}{2}-1\times\frac{1}{2}+1+0)=0.75$, and the initial weight of the "common cold" node is still $S_0(d_2)=0.5\times(1\times\frac{1}{2}+1\times\frac{1}{2}-1\times\frac{1}{2}+0+0)=0.25$ (because there is no edge between the "common cold" node and the "shaded chest radiograph" node, that is $e_{1,2}=0$), which indicates that a probability of the user suffering from the pneumonia is high; if the user inputs the information that the chest radiograph has no shadow after the chest radiograph is examined, then the weight of the "shadow on chest radiograph" node becomes −1, and back to the above mentioned process, the initial weight of the "pneumonia" node becomes $S_0(d_1)=0.5\times(1\times\frac{1}{2}+1\times\frac{1}{2}-1\times\frac{1}{2}-1+0)=-0.25$, and the initial weight of the "common cold" node is still $S_0(d_2)=0.5\times(1\times\frac{1}{2}+1\times\frac{1}{2}-1\times\frac{1}{2}+0+0)=0.25$. The result of evidence transmission indicates that a probability of the user suffering from the common cold increases.

The medical data analysis method based on the medical knowledge graph provided by the above-mentioned embodiment may be implemented by a computer program. Based on this, another embodiment of the present disclosure provides a computer device, including a memory, a processor, and a computer program stored in the memory and running on the processor, when the processor executes the program, the medical data analysis method based on the medical knowledge graph provided in the above-mentioned embodiment is implemented.

Where the processor may be may be a logical operation device with data processing capability and/or program execution capability, such as a Central Processing Unit (CPU), a Field Programmable Gate Array (FPGA), a Single-Chip Microcomputer (MCU), a Digital Signal Processor (DSP), and an Application Specific Integrated Circuit (ASIC), etc. The memory includes, but is not limited to, for example, volatile memory and/or non-volatile memory. The volatile memory may include such as Random Access Memory (RAM) and/or Cache. The non-volatile memory may include, such as Read-Only Memory (ROM), hard disk, and flash memory, etc.

The computer device provided in this embodiment comprehensively considers two aspects of symptom information of the appearing symptoms confirmed by the patient and the non-appearing symptoms confirmed by the patient. Regardless of whether the information input by the user contains a certain symptom or an examination result, the contained symptom or examination result is confirmed or denied, all symptoms and all examination results are used as the basis, and the transmission of evidence is used to determine the final weight of each node on the knowledge graph. This may accurately and efficiently provide a basis for the patient's disease prediction and effectively assist in the diagnosis of the disease. According to this, it may be realized as a general diagnosis auxiliary system covering various fields of diseases, and has high application value.

Figure 4:
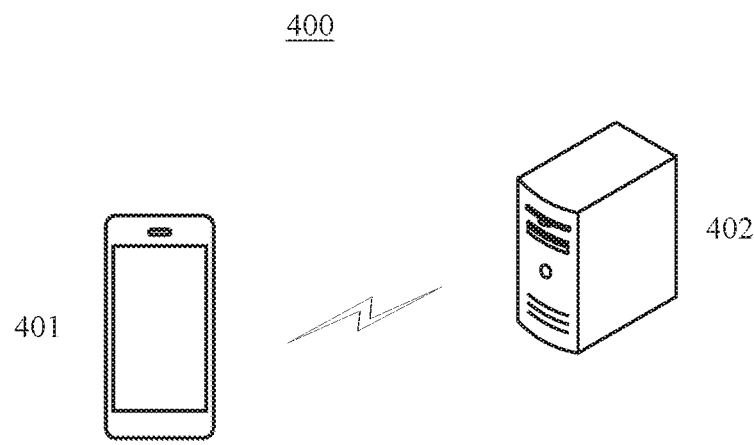
FIG. 4 shows an exemplary schematic diagram of a computer system provided by an embodiment of the present disclosure.

Another embodiment of the present disclosure provides a computer system, and FIG. 4 shows an exemplary schematic diagram of the computer system provided by the embodiment of the present disclosure.

As shown in FIG. 4, the computer system 400 may include a terminal device 401 and the computer device 402 provided in the above embodiment. The terminal device 401 is configured to send the user's symptom information and examination result information to the computer device 402, and receive an output from the computer device 402.

Where the terminal device 401 may communicate with the computer device in a variety of ways, for example, wired ways such as network cables and optical fibers, or wireless LAN ways such as Wi-Fi, BLUETOOTH™, and ZIGBEE™, or wireless wide area networks ways such as 3G, 4G, and 5G.

The terminal device 401 may be a device capable of inputting information such as a mobile phone, a tablet computer, a notebook computer, or a personal computer. The terminal device 401 may receive the user's symptom information and examination result information input by the user through its interactive device, and send it to the computer device 402. After receiving the output from the computer device 402 (for example, the disease corresponding to the N disease nodes, or the disease information corresponding to the N disease nodes, and the examination result information corresponding to the M examination result nodes), the terminal device 401 may notify the user through screen display, voice output, etc.

In a specific example, the terminal device 401 is a mobile phone, and the computer device 402 is a server. The user uses the mobile phone APP to input the symptom information and examination result information on the APP interface displayed on the touch screen of the mobile phone. The mobile phone sends the symptom information and examination result information input by the user to the server, and the server determines the initial weights of all symptom nodes and all examination result nodes on the predetermined knowledge graph according to the symptom information and examination result information, and the server returns the initial weight of each node to the mobile phone, so that the mobile phone may display the initial weight of each node to the user on the APP interface through its touch screen. At the same time, the server determines the final weight of each node on the knowledge graph based on the initial weight of each symptom node and each examination result node, and the evidence transmission of the edge of the symptom information and examination result information on the predetermined knowledge graph. After sorting the final weight of each disease node in a descending order, the disease corresponding to the top three disease nodes and their final weights are returned to the mobile phone as the result information. The mobile phone displays the result information received from the server on the APP interface to the user through its touch screen in the form of a list, bar chart, or pie chart, etc. The user may also click on the disease in the result information displayed on the APP interface through the touch screen of the mobile phone to realize subsequent operations such as disease confirmation.

In another specific example, the terminal device 401 is a personal computer, and the computer device 402 is a server. The user inputs the symptom information and examination result information through mouse clicks, keyboard operations, etc., by using the Web client of the personal computer based on the Web client interface displayed on the screen. The personal computer sends the symptom information and examination result information input by the user to the server, and the server determines the initial weights of all symptom nodes and all examination result nodes on the predetermined knowledge graph according to the symptom information and examination result information, and the server returns the initial weight of each node to the personal computer, so that the personal computer may display the initial weight of each node to the user on the Web client interface through its display screen. At the same time, the server determines the final weight of each node on the knowledge graph based on the initial weight of each symptom node and each examination result node, and the evidence transmission of the edge of the symptom information and examination result information on the predetermined knowledge graph. After sorting the final weight of each disease node in a descending order, the disease corresponding to the top three disease nodes and their final weights are returned to the personal computer as the result information. The personal computer displays the result information received from the server on the Web client interface to the user through its display screen in the form of a list, bar chart, or pie chart, etc. The user may also click on the disease in the result information displayed on the Web client interface through mouse clicks, keyboard operations, etc., to realize subsequent operations such as disease confirmation.

Figure 5:
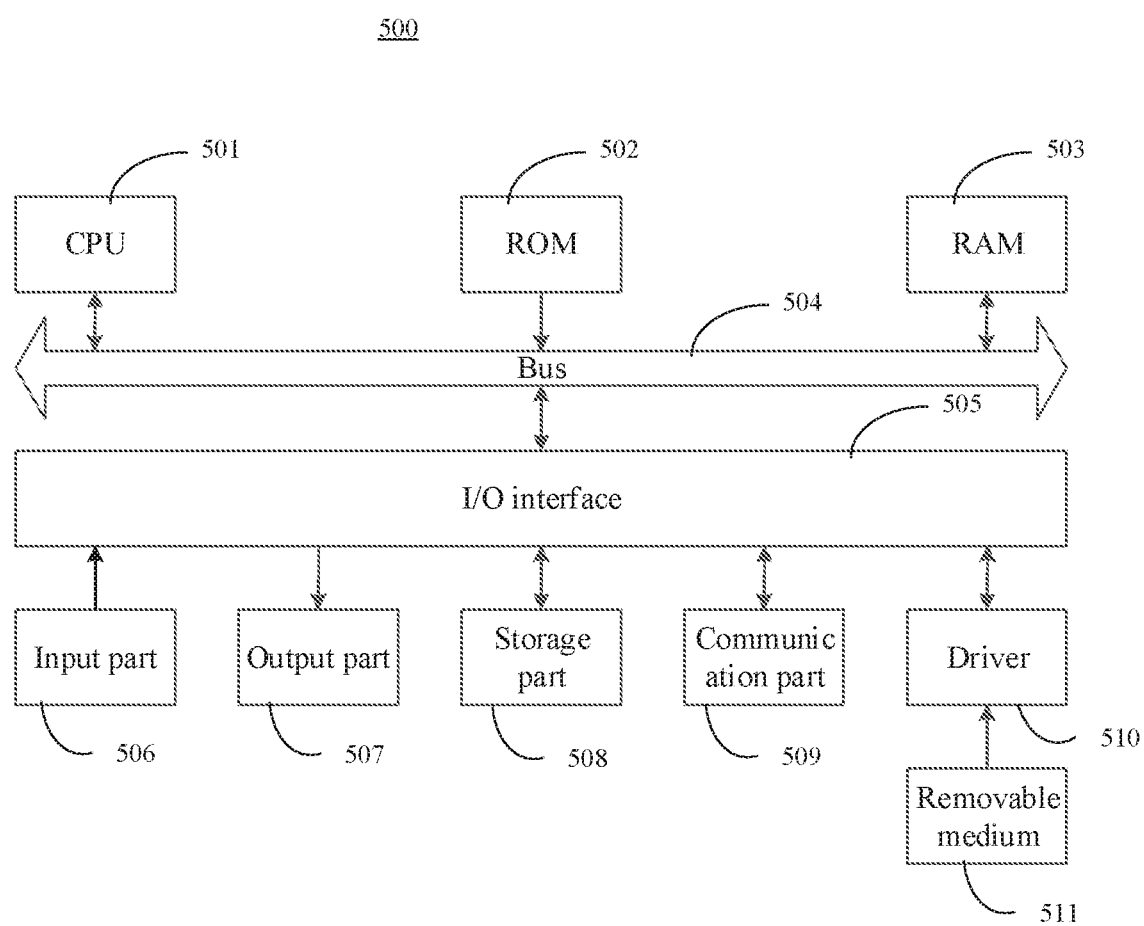
FIG. 5 shows a schematic structural diagram of a computer device provided by an embodiment of the present disclosure.

FIG. 5 shows a schematic structural diagram of a computer device provided by an embodiment of the present disclosure.

As shown in FIG. 5, a computer system suitable for implementing the computer device 500 provided by the above-mentioned embodiment includes a Central Processing Unit (CPU) 501, which may be perform various appropriate actions and processing according to a program stored in a Read-Only Memory (ROM) 502 or a program loading into the Random Access Memory (RAM) 503 from a storage part. In the RAM 503, various programs and data required for the operation of the computer system are also stored. The CPU 501, the ROM 502, and the RAM 503 are interconnected via the bus 504. An input/input (I/O) interface 505 is also connected to the bus 504.

The following components are connected to the I/O interface: an input part 506 including keyboard and mouse; an output part 507 including Liquid Crystal Display (LCD) and speakers; a storage part 508 including hard disk; and a communication part 509 including the network interface card, such as LAN card, modem etc. The communication part performs communication processing via a network such as the Internet. A driver 510 is also connected to the I/O interface as required. A removable medium 511, such as a magnetic disk, an optical disk, a magneto-optical disk, a semiconductor memory, etc., is installed on the drive as required, so that the computer program read from it is installed into the storage part as required.

In particular, according to this embodiment, the process described in the above flowchart may be implemented as a computer software program. For example, this embodiment includes a computer program product, which includes a computer program tangibly contained on a computer-readable medium, and the above-mentioned computer program includes program code for executing the method shown in the flowchart. In such an embodiment, the computer program may be downloaded and installed from the network through the communication part, and/or installed from a removable medium.

The flowcharts and schematic diagrams in the accompanying drawings illustrate the possible implementation architecture, functions, and operations of the system, method, and computer program product of this embodiment. In this regard, each block in the flowchart or schematic diagram may represent a module, program segment, or part of the code, and the above-mentioned module, program segment, or part of the code contains one or more executable instructions for realizing the specified logic function. It should also be noted that, in some alternative implementations, the functions marked in the block may also occur in a different order from the order marked in the drawings. For example, two blocks shown in succession may actually be executed substantially in parallel, or they may sometimes be executed in the reverse order, depending on the functions involved. It should also be noted that each block in the schematic and/or flowchart, and the combination of the blocks in the schematic and/or flowchart, may be implemented by a dedicated hardware-based system that performs the specified functions or operations, or it may be realized by a combination of dedicated hardware and computer instructions.

As another aspect, the embodiments of the present disclosure also provide a non-volatile computer storage medium, and the non-volatile computer storage medium may be the non-volatile computer storage medium included in the above-mentioned device in the above-mentioned embodiment, and it may also be a non-volatile computer storage medium that exists alone and is not assembled into the terminal. The above-mentioned non-volatile computer storage medium stores one or more programs, and when the above-mentioned one or more programs are executed by a device, the above-mentioned device executes the medical data analysis method based on the medical knowledge graph provided by the above-mentioned embodiment.

It should be noted that in the description of the present disclosure, the terms "including", "comprising" or any other variations thereof are intended to cover non-exclusive inclusion, so that a process, method, article, or device including a series of elements not only includes those elements, but also include other elements that are not explicitly listed, or elements inherent to the process, method, article, or device. If there are no more restrictions, the element defined by the sentence "including a . . . " does not exclude the existence of other same elements in the process, method, article, or device including the element.

Obviously, the above-mentioned embodiments of the present disclosure are merely examples to clearly illustrate the present disclosure, and are not intended to limit the implementation of the present disclosure. For those of ordinary skill in the art, they may also do other modifications of changes in different forms on the basis of the foregoing description. It is not possible to list all the implementations here. Any obvious modifications or changes derived from the technical solutions of the present disclosure are still within the protection scope of the present disclosure.

What is claimed is:

1. A medical data analysis method based on a medical knowledge graph, executed by a computer device, the method comprising:

acquiring symptom information of a patient and examination result information of a patient;

accessing a predetermined knowledge graph, the predetermined knowledge graph comprising a plurality of nodes and a plurality of edges, the plurality of nodes comprising a plurality of first nodes configured to characterize multiple types of symptoms, a plurality of second nodes configured to characterize multiple types of examination results, and a plurality of third nodes configured to characterize multiple types of diseases, the plurality of edges configured to characterize relationships between the symptoms and the diseases, and relationships between the diseases and the examination results;

determining an initial weight of each of the plurality of first nodes and the plurality of second nodes of the predetermined knowledge graph according to the symptom information and the examination result information;

transmitting evidence through the plurality of edges on the predetermined knowledge graph based on the initial weight of each of the plurality of first nodes and the plurality of second nodes, to determine a final weight of each of the plurality of nodes, which comprises:

performing iterative calculation on the weight of each of the plurality of nodes using a random walk algorithm based on the initial weight of each of the plurality of first nodes and the plurality of second nodes to realize that the symptom information and the examination result information are served as initial evidences to be transmitted through the plurality of edges on the predetermined knowledge graph, so as to determine a final weight of each of the plurality of nodes, wherein the iterative calculation includes for a $j^{th}$ third node $d_j$ in the plurality of third nodes, an initial weight is:

$$S_0(d_j) = \lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right);$$

a weight calculated in the $(t+1)^{th}$ iteration is:

$$S_{t+1}(d_j) = (1-\lambda)S_t(d_j) + \lambda \left( \sum_{i=1}^{t} S_t(s_i) \times \frac{e_{i,j}}{\sum_{j=1}^{J} e_{i,j}} + \sum_{k=1}^{K} S_t(c_k) \times \frac{e_{k,j}}{\sum_{j=1}^{J} e_{k,j}} \right);$$

for an $i^{th}$ first node $s_i$ in the plurality of first nodes, a weight calculated in the $(t+1)^{th}$ iteration is:

$$S_{t+1}(s_i) = (1-\lambda)S_t(s_i) + \lambda \sum_{j=1}^{J} S_t(d_j) \times \frac{e_{i,j}}{\sum_{i=1}^{I} e_{i,j}};$$

for a $k^{th}$ second node $c_k$ in the plurality of second nodes, a weight calculated in the $(t+1)^{th}$ iteration is:

$$S_{t+1}(c_k) = (1-\lambda)S_t(s_i) + \lambda \sum_{j=1}^{J} S_t(d_j) \times \frac{e_{k,j}}{\sum_{k=1}^{K} e_{k,j}};$$

wherein $t=0,1,\ldots,T-1$; $\lambda$ is a predetermined harmonic parameter; $S_0(s_i)$ is an initial weight of the first node $s_i$; $S_0(c_k)$ is an initial weight of the second node $c_k$; when there is an edge between the first node $s_i$ and the third node $d_j$, the $e_{i,j}$ is set to 1, when there is no edge between the first node $s_i$ and the third node $d_j$, the $e_{i,j}$ is set to 0; when there is an edge between the second node $c_k$ and the third node $d_j$, the $e_{k,j}$ is set to 1, when there is no edge between the second node $c_k$ and the third node $d_j$, the $e_{k,j}$ is set to 0; I, K, J is the number of the plurality of first nodes, the number of the plurality of second nodes, and the number of the plurality of third nodes, respectively, and T is the maximum number of iterations;

determining prediction information for the symptom information and the examination result information based on the final weight of each of the plurality of nodes, wherein the prediction information comprises an instruction to a user for a further examination, comprising a chest radiograph examination or a routine blood examination;

updating one or more weights of one or more nodes in the knowledge graph based on a result of the further examination and re-determining the prediction information after the updating, wherein prior to acquiring symptom information and examination result information of a patient, the method further comprises:

extracting symptom information, disease information, examination result information, relationship information between the symptoms and the diseases, and a relationship information between the diseases and the examination results from medical data; and constructing the plurality of first nodes, the plurality of third nodes, and the plurality of second nodes based on the symptom information, the disease information, and the examination result information, and constructing the plurality of edges among the plurality of nodes based on the relationship information between the symptoms and diseases and the relationship information between the diseases and the examination results, so that the predetermined knowledge graph is formed by the plurality of nodes and the plurality of edges.

2. The method according to claim 1, wherein the determining an initial weight of each of the plurality of first nodes and the plurality of second nodes of the predetermined knowledge graph according to the symptom information and the examination result information comprises:

for a first node in the plurality of first nodes for a confirmed symptom in the symptom information and a second node in the plurality of second nodes for a confirmed examination result in the examination result information, an initial weight is set to $\alpha_1$;

for a first node in the plurality of first nodes for a denial symptom in the symptom information and a second node in the plurality of second nodes for a denial examination result in the examination result information, an initial weight is set to $\alpha_2$; and for other first nodes in the plurality of first nodes except the first node for the confirmed symptom and for the denial symptom, and other second nodes in the plurality of second nodes except the second node for the confirmed examination result and for the denial examination result, an initial weight is set to $\alpha_3$.

3. The method according to claim 2, wherein the values of $\alpha_1$, $\alpha_2$, and $\alpha_3$ are respectively set as $\alpha_1=1$, $\alpha_2=-1$, $\alpha_3=0$.

4. The method according to claim 1, wherein the value of the harmonic parameter $\lambda$ is set to $\lambda \in (0,1)$.

5. The method according to claim 1, wherein the termination condition of the iterative calculation comprises:

reaching maximum number of iterations; or the rate of change of the weight of each of the plurality nodes is lower than a predetermined threshold.

6. The method according to claim 1, wherein the determining prediction information for the symptom information and the examination result information based on the final weight of each of the plurality of nodes comprises:

sorting the plurality of third nodes according to the final weight in a descending order, and outputting disease information for the top N third nodes as the prediction information for the symptom information and the examination result information; or sorting the plurality of third nodes according to the final weight in an ascending order, and outputting disease information for third nodes ranked in the bottom N as the prediction information for the symptom information and the examination result information, wherein N is a positive integer.

7. The method according to claim 1, wherein the determining prediction information for the symptom information and the examination result information based on the final weights of the plurality of nodes comprises:

determining second nodes in the plurality of second nodes that are for the examination result not contained in the examination result information as candidate second nodes;

sorting the candidate second nodes according to the final weight in a descending order, and outputting the examination information for the top M candidate second nodes as the prediction information for the symptom information and the examination result information; or sorting the candidate second nodes according to the final weight in an ascending order, and outputting the examination information for the candidate second nodes ranked as bottom M as the prediction information for the symptom information and the examination result information, wherein M is a positive integer.

8. A computer device comprising a memory, a processor, and a computer program stored on the memory and running on the processor, wherein the processor is configured to execute the following steps when the computer program is loaded:

acquiring symptom information of a patient and examination result information of a patient;

accessing a predetermined knowledge graph, the predetermined knowledge graph comprising a plurality of nodes, the plurality of nodes comprising a plurality of first nodes configured to characterize multiple types of symptoms, a plurality of second nodes configured to characterize multiple types of examination results, a plurality of third nodes configured to characterize multiple types of diseases, and a plurality of edges configured to characterize the relationship between symptoms and diseases, and the relationship between diseases and examination results;

determining an initial weight of each of the plurality of first nodes and the plurality of second nodes of the predetermined knowledge graph according to the symptom information and the examination result information;

transmitting evidence through the plurality of edges on the predetermined knowledge graph based on the initial weight of each of the plurality of first nodes and the plurality of second nodes, to determine a final weight of each of the plurality of nodes, which comprises:

performing iterative calculation on the weight of each of the plurality of nodes using a random walk algorithm based on the initial weight of each of the plurality of first nodes and the plurality of second nodes to realize that the symptom information and the examination result information are served as initial evidences to be transmitted through the plurality of edges on the predetermined knowledge graph, so as to determine a final weight of each of the plurality of nodes, wherein the iterative calculation includes for a $j_{th}$ third node $d_j$ in the plurality of third nodes, an initial weight is:

$$S_0(d_j) = \lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right);$$

a weight calculated in the $(t+1)^{th}$ iteration is:

$$S_{t+1}(d_j) = (1-\lambda)S_t(d_j) + \lambda\left(\sum_{i=1}^{I} S_t(s_i) \times \frac{e_{i,j}}{\sum_{j=1}^{J} e_{i,j}} + \sum_{k=1}^{K} S_t(c_k) \times \frac{e_{k,j}}{\sum_{j=1}^{J} e_{k,j}}\right);$$

for an $i^{th}$ first node $s_i$ in the plurality of first nodes, a weight calculated in the $(t+1)^{th}$ iteration is:

$$S_{t+1}(s_i) = (1-\lambda)S_t(s_i) + \lambda\sum_{j=1}^{J} S_t(d_j) \times \frac{e_{i,j}}{\sum_{i=1}^{I} e_{i,j}};$$

for a $k^{th}$ second node $c_k$ in the plurality of second nodes, a weight calculated in the $(t+1)^h$ iteration is:

$$S_{t+1}(s_i) = (1-\lambda)S_t(s_i) + \lambda\sum_{j=1}^{J} S_t(d_j) \times \frac{e_{k,j}}{\sum_{k=1}^{K} e_{k,j}};$$

wherein t=0,1, . . . ,T−1; λ is a predetermined harmonic parameter; $S_0(s_i)$ is an initial weight of the first node $s_i$; $S_0(c_k)$ is an initial weight of the second node $c_k$; when there is an edge between the first node $s_i$ and the third node $d_j$, the $e_{i,j}$ is set to 1, when there is no edge between the first node $s_i$ and the third node $d_j$, the $e_{i,j}$ is set to 0; when there is an edge between the second node $c_k$ and the third node $d_j$, the $e_{k,j}$ is set to 1, when there is no edge between the second node $c_k$ and the third node $d_j$, the $e_{k,j}$ is set to 0; I, K, J is the number of the plurality of first nodes, the number of the plurality of second nodes, and the number of the plurality of third nodes, respectively, and T is the maximum number of iterations;

determining prediction information for the symptom information and the examination result information based on the final weights of each of the plurality of nodes, wherein the prediction information comprises an instruction to a user for a further examination, comprising a chest radiograph examination or a routine blood examination; and updating one or more weights of one or more nodes in the knowledge graph based on a result of the further examination and re-determining the prediction information after the updating, wherein prior to acquiring symptom information and examination result information of a patient, the method further comprises:

extracting symptom information, disease information, examination result information, relationship information between the symptoms and the diseases, and a relationship information between the diseases and the examination results from medical data; and constructing the plurality of first nodes, the plurality of third nodes, and the plurality of second nodes based on the symptom information, the disease information, and the examination result information, and constructing the plurality of edges among the plurality of nodes based on the relationship information between the symptoms and diseases and the relationship information between the diseases and the examination results, so that the predetermined knowledge graph is formed by the plurality of nodes and the plurality of edges.

9. The computer device according to claim 8, wherein the processor is configured to execute the following steps when the computer program is loaded:

for a first node in the plurality of first nodes for a confirmed symptom in the symptom information and a second node in the plurality of second nodes for a confirmed examination result in the examination result information, an initial weight is set to $\alpha_1$;

for a first node in the plurality of first nodes for a denial symptom in the symptom information and a second node in the plurality of second nodes for a denial examination result in the examination result information, an initial weight is set to $\alpha_2$; and for other first nodes in the plurality of first nodes except the first node for the confirmed symptom and for the denial symptom, and other second nodes in the plurality of second nodes except the second node for the confirmed examination result and for the denial examination result, an initial weight is set to $\alpha_3$.

10. The computer device according to claim 9, wherein the values of $\alpha_1$, $\alpha_2$ and $\alpha_3$ are respectively set as $\alpha_1=1$, $\alpha_2=-1$, $\alpha_3=0$.

11. The computer device according to claim 8, wherein the value of the harmonic parameter λ is set to $\lambda \in (0,1)$.

12. The computer device according to claim 8, wherein the termination condition of the iterative calculation comprises:

reaching a maximum number of iterations; or the rate of change of the weight of each of the plurality of nodes is lower than a predetermined threshold.

13. The computer device according to claim 8, wherein when the computer program is loaded, the processor is configured to execute:

sorting the plurality of third nodes according to the final weight from largest to smallest, and outputting disease information for the top N third nodes as the prediction information for the symptom information and the examination result information; or sorting the plurality of third nodes according to the final weight from smallest to largest, and outputting disease information for third nodes ranked in the bottom N as the prediction information for the symptom information and the examination result information, wherein N is a positive integer.

14. A computer system comprising a terminal device and the computer device according to claim 8, the terminal device being configured to send user's symptom information and examination result information to the computer device, and receive output from the computer device.

15. A non-transitory computer-readable storage medium on which a computer program is stored, wherein the following steps are executed when the computer program is loaded by a processor:

acquiring symptom information of a patient and examination result information of a patient;

accessing a predetermined knowledge graph, the predetermined knowledge graph comprising a plurality of nodes, the plurality of nodes comprising a plurality of first nodes configured to characterize multiple types of symptoms, a plurality of second nodes configured to characterize multiple types of examination results, a plurality of third nodes configured to characterize multiple types of diseases, and a plurality of edges configured to characterize the relationship between symptoms and diseases, and the relationship between diseases and examination results;

determining an initial weight of each of the plurality of first nodes and the plurality of second nodes of the predetermined knowledge graph according to the symptom information and the examination result information;

transmitting evidence through the plurality of edges on the predetermined knowledge graph based on the initial weight of each of the plurality of first nodes and the plurality of second nodes, to determine a final weight of each of the plurality of nodes, which comprises:

performing iterative calculation on the weight of each of the plurality of nodes using a random walk algorithm based on the initial weight of each of the plurality of first nodes and the plurality of second nodes to realize that the symptom information and the examination result information are served as initial evidences to be transmitted through the plurality of edges on the predetermined knowledge graph, so as to determine a final weight of each of the plurality of nodes, wherein the iterative calculation includes for a $j_{th}$ third node $d_j$ in the plurality of third nodes, an initial weight is:

$$S_0(d_j) = \lambda \left( \sum_{i=1}^{I} S_0(s_i) \times \frac{e_{i,j}}{\sum_{j=1}^{J} e_{i,j}} + \sum_{k=1}^{K} S_0(c_k) \times \frac{e_{k,j}}{\sum_{j=1}^{J} e_{k,j}} \right);$$

and a weight calculated in the $(t+1)^{th}$ iteration is:

$$S_{t+1}(d_j) = (1-\lambda)S_t(d_j) + \lambda \left( \sum_{i=1}^{I} S_t(s_i) \times \frac{e_{i,j}}{\sum_{j=1}^{J} e_{i,j}} + \sum_{k=1}^{K} S_t(c_k) \times \frac{e_{k,j}}{\sum_{j=1}^{J} e_{k,j}} \right);$$

for an $i^{th}$ first node $s_i$ in the plurality of first nodes, a weight calculated in the $(t+1)^{th}$ iteration is:

$$S_{t+1}(s_i) = (1-\lambda)S_t(s_i) + \lambda \sum_{j=1}^{J} S_t(d_j) \times \frac{e_{i,j}}{\sum_{i=1}^{I} e_{i,j}};$$

for a $k^{th}$ second node $c_k$ in the plurality of second nodes, a weight calculated in the $(t+1)^{th}$ iteration is:

$$S_{t+1}(c_k) = (1-\lambda)S_t(c_k) + \lambda \sum_{j=1}^{J} S_t(d_j) \times \frac{e_{i,j}}{\sum_{k=1}^{K} e_{i,j}};$$

wherein $t=0,1,\ldots,T-1$; $\lambda$ is a predetermined harmonic parameter; $S_0(s_i)$ is an initial weight of the first node $s_i$; $S_0(c_k)$ is an initial weight of the second node $c_k$; when there is an edge between the first node $s_i$ and the third node $d_j$, the $e_{i,j}$ is set to 1, when there is no edge between the first node $s_i$ and the third node $d_j$, the $e_{i,j}$ is set to 0; when there is an edge between the second node $c_k$ and the third node $d_j$, the $e_{k,j}$ is set to 1, when there is no edge between the second node $c_k$ and the third node $d_j$, the $e_{k,j}$ is set to 0; I, K, J is the number of the plurality of first nodes, the number of the plurality of second nodes, and the number of the plurality of third nodes, respectively, and T is the maximum number of iterations;

determining prediction information for the symptom information and the examination result information based on the final weight of each of the plurality of nodes, wherein the prediction information comprises an instruction to a user for a further examination, comprising a chest radiograph examination or a routine blood examination; and updating one or more weights of one or more nodes in the knowledge graph based on a result of the further examination and re-determining the prediction information after the updating, wherein prior to acquiring symptom information and examination result information of a patient, the method further comprises:

extracting symptom information, disease information, examination result information, relationship information between the symptoms and the diseases, and a relationship information between the diseases and the examination results from medical data; and constructing the plurality of first nodes, the plurality of third nodes, and the plurality of second nodes based on the symptom information, the disease information, and the examination result information, and constructing the plurality of edges among the plurality of nodes based on the relationship information between the symptoms and diseases and the relationship information between the diseases and the examination results, so that the predetermined knowledge graph is formed by the plurality of nodes and the plurality of edges.

* * * * *